United States Patent [19]
Gagner

[11] Patent Number: 5,634,882
[45] Date of Patent: Jun. 3, 1997

[54] ABDOMEN SUSPENDING DEVICE

[76] Inventor: Michel Gagner, 159 Rolland-Jeanneau, Verdun Qué., Canada

[21] Appl. No.: 426,486

[22] Filed: Apr. 20, 1995

Related U.S. Application Data

[63] Continuation of Ser. No. 897,804, Jun. 12, 1992, abandoned.

[30] Foreign Application Priority Data

May 7, 1992 [CA] Canada .......................... 2068121

[51] Int. Cl.⁶ .................................................. A61B 1/22
[52] U.S. Cl. .................. 600/201; 600/206; 600/208; 600/209; 600/235; 600/227
[58] Field of Search .................................... 600/204, 206, 600/208, 209, 235, 210, 227, 201

[56] References Cited

U.S. PATENT DOCUMENTS

| | | | |
|---|---|---|---|
| 343,145 | 6/1886 | Walker | 606/106 |
| 1,944,009 | 1/1934 | Homer | 128/20 |
| 3,099,544 | 7/1963 | Sheesley | 101/491 |
| 3,196,865 | 7/1965 | Rose | 128/20 |
| 3,288,131 | 11/1966 | Garland | 128/20 |
| 3,710,783 | 1/1973 | Jascalevich | 128/20 |
| 3,810,462 | 5/1974 | Szpur | 128/20 |
| 3,995,151 | 11/1976 | Nordeen et al. | 240/10 A |
| 4,143,652 | 3/1979 | Meier et al. | 128/20 |
| 4,365,632 | 12/1982 | Kortum | 606/191 |
| 4,380,999 | 4/1983 | Healy | 128/20 |
| 4,428,746 | 1/1984 | Mendez | 604/8 |
| 4,616,633 | 10/1986 | Vargas Garcia | |
| 4,616,637 | 10/1986 | Caspari et al. | 128/84 R |
| 4,622,955 | 11/1986 | Fakhrai | 128/20 |
| 4,706,671 | 11/1987 | Weinrib | 604/104 X |
| 4,959,067 | 9/1990 | Muller | |
| 4,994,069 | 2/1991 | Ritchart et al. | 606/191 |
| 5,065,739 | 11/1991 | Forrest et al. | 128/20 |
| 5,106,369 | 4/1992 | Christmas | 128/20 X |
| 5,307,790 | 5/1994 | Byrne | |
| 5,375,591 | 12/1994 | Mouret | |
| 5,398,671 | 3/1995 | Ortiz et al. | |
| 5,460,169 | 10/1995 | Mouret | |
| 5,501,653 | 3/1996 | Chin | 600/204 |

FOREIGN PATENT DOCUMENTS

| | | | |
|---|---|---|---|
| 0255533 | 7/1926 | United Kingdom | 606/191 |
| 91/14392 | 10/1991 | WIPO | |

*Primary Examiner*—Richard J. Apley
*Assistant Examiner*—Beverly M. Flanagan
*Attorney, Agent, or Firm*—Merchant, Gould, Smith, Edell, Welter & Schmidt

[57] ABSTRACT

The present invention relates to a method and device for suspending the abdominal wall of a patient. The device is formed of a substantially rigid rod comprising a first section having a free end and bent to define either a conical helix or a planar serpentine figure. A second section of the rod is used as a pulling member. In accordance with the method of the invention, to suspend the abdominal wall of a patient, (a) an incision is cut in the patient's abdominal wall, (b) the free end of the first rod section is inserted in the incision and the first rod section slid in this incision until it is completely introduced in the patient's abdominal cavity, and (c) the second rod section, situated on the outside of the abdominal wall, is pulled to apply the first rod section on the inner face of the patient's abdominal wall and then to suspend this abdominal wall.

4 Claims, 2 Drawing Sheets

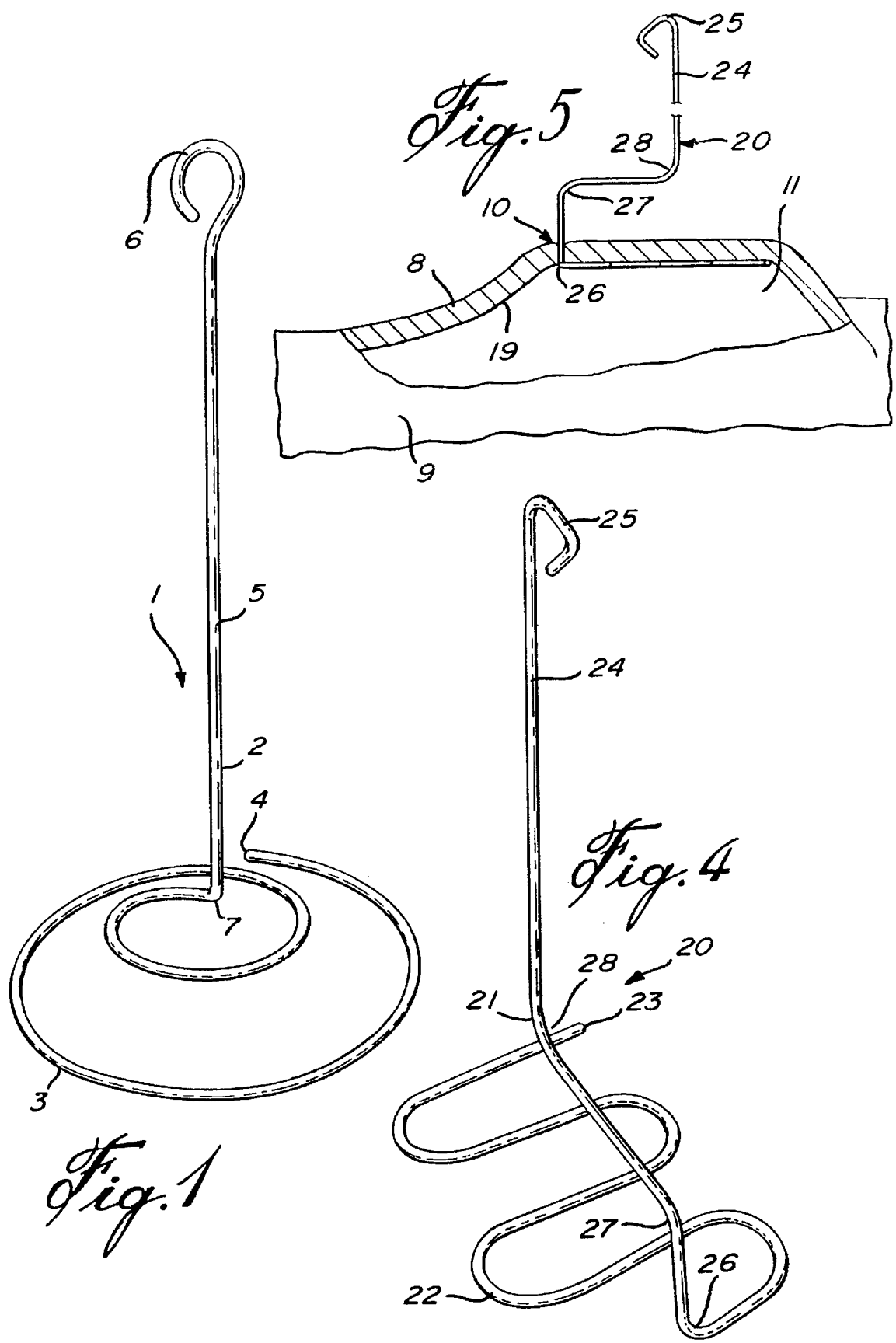

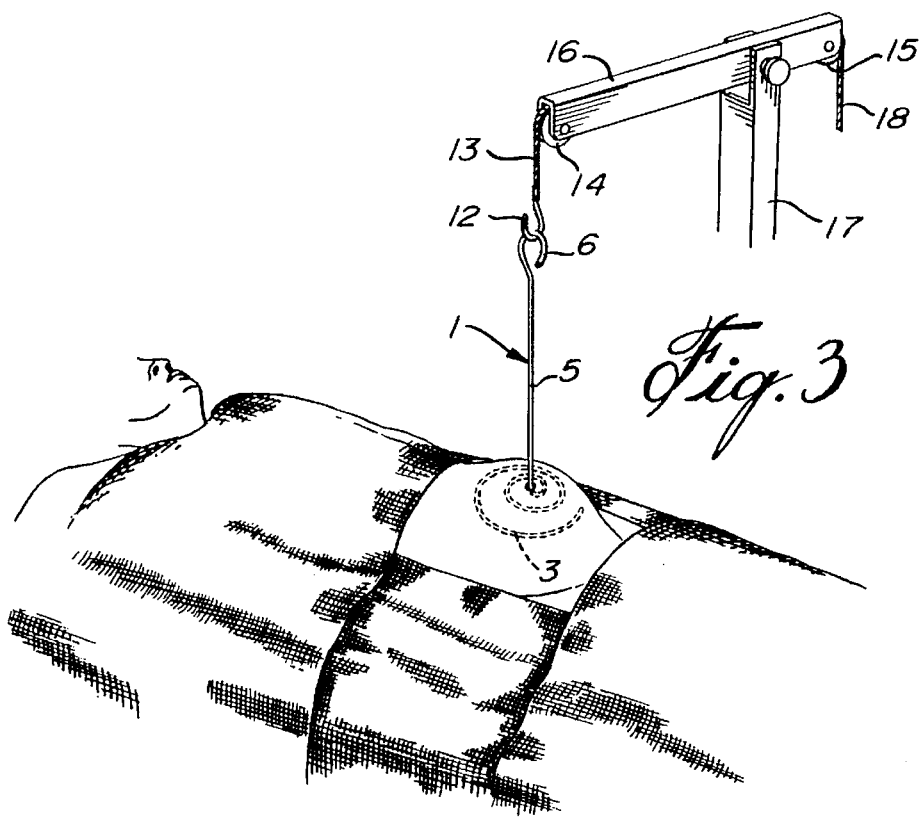
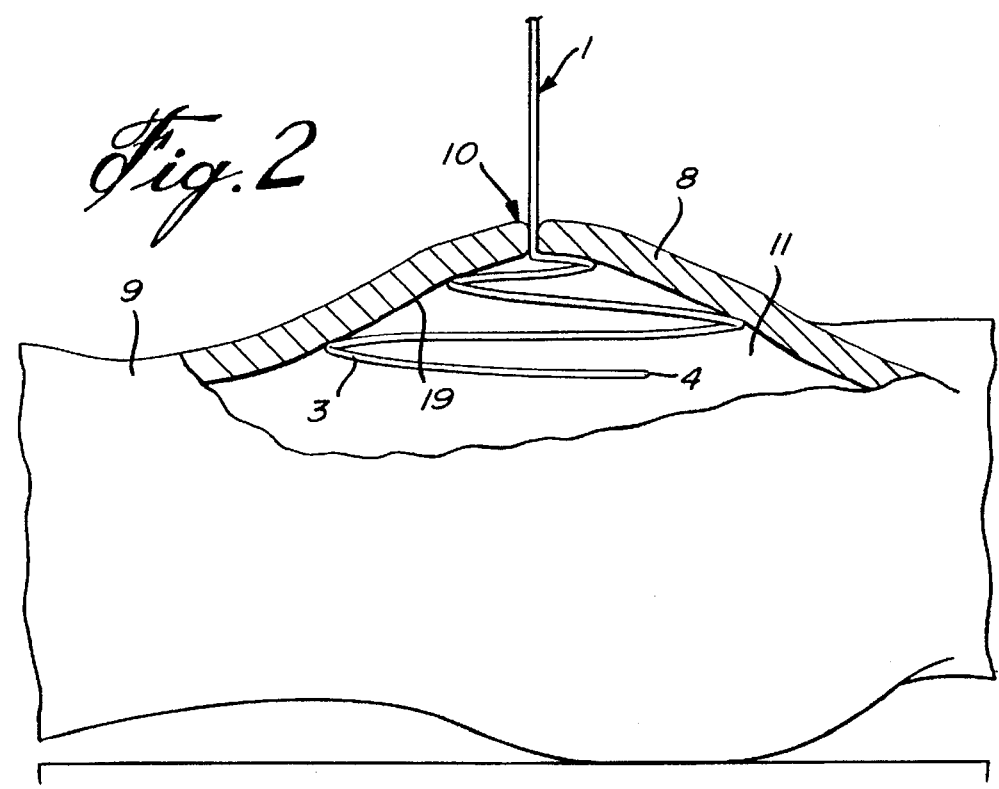

ABDOMEN SUSPENDING DEVICE

This is a continuation, of application Ser. No. 07/897,804 filed Jun. 12, 1992, now abandoned.

BACKGROUND OF THE INVENTION

1. Field of the invention

The present invention relates to a method and device for mechanically suspending the abdominal wall of a patient during a surgical operation, for example during a laparascopic operation.

2. Brief description of the prior art

During a laparascopic operation, the abdomen of the patient is conventionally inflated with carbonic gas ($CO_2$) to enable displacement of the instruments in the patient's abdominal cavity.

A drawback of this conventional method is that any instruments, such as a catheter, used by the surgeon during the operation must be introduced in the patient's abdominal cavity through a gas-tight trocar to prevent deflating of the abdomen. Therefore, a surgical instrument that cannot be introduced in the abdominal cavity of the patient through such a gas-tight trocar cannot be used during the operation. One skilled in the art can appreciate that this drawback considerably limits the number and type of instruments employed during a laparascopic operation.

OBJECT OF THE INVENTION

An object of the present invention is to overcome the above mentioned drawback of the prior art by mechanically pulling the abdominal wall of the patient, instead of inflating the abdomen.

SUMMARY OF THE INVENTION

In accordance with the present invention, there is provided a device for pulling a tissue wall of a patient's body, comprising an elongate, generally thin member comprising a first free end and a second end, which elongate member being bent into a figure capable of being applied to a rear face of the patient's tissue wall, and a pulling member secured to the second end of the elongate member. In order to pull the patient's tissue wall, (a) an incision is cut in the tissue of this wall, (b) the free end of the elongate member is inserted in the incision and the elongate member slid in this incision until it is completely located behind the tissue wall, and (c) the pulling member, still located in front of the wall, is pulled to apply the figure on the rear face of the tissue wall and then to pull the patient's tissue wall.

Also in accordance with the present invention, there is provided a device for suspending the abdominal wall of a patient lying on his back, comprising an elongate, generally thin member comprising a first free end and a second end, this elongate member being bent into a figure capable of being applied to the inner face of the patient's abdominal wall, and a pulling member secured to the second end of the elongate member. In order to suspend the patient's abdominal wall, (a) an incision is cut in this abdominal wall, (b) the free end of the elongate member is inserted in the incision and the elongate member slid in the incision until it is completely introduced in the patient's abdominal cavity, and (c) the pulling member, still located on the outside of the abdominal wall, is pulled upwardly to apply the figure on the inner face of the abdominal wall and then to suspend that abdominal wall.

According to preferred embodiments of the present invention, the elongate member is slightly flexible, and the above mentioned figure is a spiral, more specifically a conical helix. This figure may also be a planar serpentine figure. Preferably, a single rod forms both the elongate and pulling members.

The present invention further relates to a method of pulling a tissue wall of a patient's body, comprising the steps of cutting an incision in the tissue of the patient's wall, sliding an elongate, generally thin member, bent into a figure capable of being applied to a rear face of the patient's tissue wall, in the incision to position this elongate member behind the patient's tissue wall, and pulling the elongate member to apply the figure on the rear face of the tissue wall and then to pull the patient's tissue wall.

The objects, advantages and other features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 1 is a perspective view of a first embodiment of the abdomen suspending device in accordance with the present invention, comprising an elongate rod section defining a conical helix;

FIG. 2 is a side elevational view, partially cross sectional, of the device of FIG. 1, of which the elongate rod section has been introduced in the abdominal cavity of a patient;

FIG. 3 is a perspective view showing the device of FIG. 1 used to suspend the abdominal wall of the patient;

FIG. 4, which is disposed on the same sheet of formal drawings as FIG. 1, is a perspective view of a second embodiment of the device in accordance with the present invention, comprising an elongate rod section defining a planar serpentine figure; and FIG. 5, disposed on the same sheet of formal drawings as FIGS. 1 and 4, is a side elevational view, partially cross sectional, of the device of FIG. 4, of which the elongate rod section has been introduced in the abdominal cavity of a patient.

DETAILED DESCRIPTION OF THE PREFERRED EMBODIMENTS

The first embodiment of the device in accordance with the present invention is generally identified by the reference numeral 1 in FIGS. 1 to 3.

The device 1 is formed, as illustrated in FIG. 1, of a generally thin and slightly flexible rod 2 made for example of stainless steel and having a circular cross section.

The rod 2 comprises a first rod section 3 bent into a spiral figure. More specifically, the bent rod section 3 generally defines a conical helix. The rod section 3 also comprises a free end 4.

The rod 2 is also formed with a second rod section 5. Rod section 5 is straight but has a free end bent to define a hook 6. As can be seen in FIG. 1, the straight rod section 5 is aligned with the axis of the spiral, more specifically the conical helix of rod section 3.

Between sections 3 and 5, the rod 2 is bent at 90° (see point 7 in FIG. 1).

To install the device 1, a small incision 10 is first made in the abdominal wall 8 of the patient 9 (see FIG. 2), in the region of the umbilicus. Then, the free end 4 of the rod section 3 is inserted in the incision 10. Rod section 3 is slid in the incision 10 until this section 3 is completely introduced in the patient's abdominal cavity 11.

As illustrated in FIG. 3, the hook 6 is then engaged with another hook 12 attached to one end of a small rope 13. The rope 13 is inserted in the grooves of a pair of pulleys 14 and 15 pivotally mounted at the respective ends of a horizontal support member 16 itself fixedly mounted on a vertical post 17. A weight (not shown) is attached to the other end 18 of the rope 13 to stretch that rope. As shown in FIG. 3, the pulley 14 is positioned over the patient's abdomen.

In operation, the weight (not shown) attached to the end 18 of the rope 13 will stretch that rope to pull the rod section 3, situated in the patient's abdominal cavity 11, through the hook 12, the hook 6, and the rod section 5. The figure defined by the rod section 3 will be applied to the inner face of the patient's abdominal wall 8 and the tension in the small rope 13 will suspend this abdominal wall 8. As can be appreciated, the straight rod section 5 serves as a member for pulling the rod section 3.

Accordingly, the abdominal wall 8 of the patient 9 is suspended by means of a mechanical device 1. Therefore, it is no longer necessary to hold a gas pressure within the abdominal cavity 11 whereby the drawback discussed in the preamble of the present disclosure is overcome.

The second embodiment of the abdomen suspending device in accordance with the present invention is generally identified by the reference numeral 20 in FIGS. 4 and 5.

The device 20 is formed, as illustrated in FIG. 4, of a generally thin and slightly flexible rod 21 made for example of stainless steel and having a circular cross section.

The rod 21 comprises a first rod section 22 bent into a planar serpentine figure. The rod section 22 includes a free end 23.

The rod 21 is also formed with a second rod section 24. Rod section 24 is straight but has a free end bent to define a hook 25. As can be seen in FIG. 1, the straight rod section 24 has a longitudinal axis passing through the center of the serpentine figure defined by rod section 22.

Between rod sections 22 and 24, the rod 21 is bent a first time at 90° (see point 26 in FIGS. 4 and 5). It is also bent a second and a third time at 90° (see points 27 and 28 in FIGS. 4 and 5) to align the straight rod section 24 with the center of the serpentine figure. This will enable application of a pulling force centered on the serpentine figure of rod section 22.

To install the device 20, the free end 23 of the rod section 22 is inserted in the small incision 10 (FIG. 5). Serpentine rod section 22 is then slid in the incision 10 until this section 22 is completely introduced in the patient's abdominal cavity 11.

In the same manner as the device 1 (see. FIG. 3), the hook 25 can be engaged with the hook 12 attached to one end of the small rope 13 which itself is inserted in the grooves of the pulleys 14 and 15. Again, the pulley 14 is positioned over the patient's abdomen. The weight (not shown) attached to the end 18 of the rope 13 will stretch that rope to pull the serpentine rod section 22, situated in the patient's abdominal cavity 11 (FIG. 5), through the hook 12, the hook 25, and the rod section 24. The straight rod section 24 therefore serves as a member for pulling the serpentine rod section 22 situated within the abdominal cavity 11. The serpentine figure defined by the rod section 22 will be applied to the inner face 19 of the patient's abdominal wall 8 and the tension in the small rope 13 will suspend this abdominal wall 8.

Again, the abdominal wall 8 of the patient 9 is suspended by means of a mechanical device 1. Therefore, it is no longer necessary to hold a gas pressure within the abdominal cavity 11 whereby the drawback discussed in the preamble of the present disclosure is overcome.

As can be appreciated by one skilled in the art, the first embodiment 1 (FIGS. 1–3) will enable suspension of the abdominal wall 8 around the umbilicus (see FIG. 2). The embodiment 20 (FIGS. 4 and 5) of the abdomen suspending device will enable suspension of the abdominal wall 8 on one side of the umbilicus (see FIG. 5).

Although the present invention has been described hereinabove by way of preferred embodiments thereof, these embodiments can be modified at will, within the scope of the appended claims, without departing from the spirit and nature of the present invention.

The embodiments of the invention in which an exclusive property or privilege is claimed are defined as follows:

1. A surgical abdominal wall pulling device comprising:

a pulling member;

an elongate, generally thin member forming a generally conical helix and comprising a first free end and a second end, said generally conical helix having an apex, and the second end of the elongate, generally thin member being situated at the apex of said generally conical helix and connected to said pulling member; and wherein, to pull the abdominal wall of a patient, (a) an incision is cut in the patient's abdominal wall, (b) the first free end of the elongate, generally thin member is inserted in the incision and the elongate, generally thin member slid in said incision until it is completely introduced in the patient's abdominal cavity, and (c) said pulling member, still located on the outside of the patient's abdominal wall is pulled to apply said generally conical helix on the inner face of the patient's abdominal wall and then to pull the patient's abdominal wall.

2. A surgical abdominal wall pulling device according to claim 1, wherein said pulling member and the elongate, generally thin member are formed by a single, generally thin rod.

3. A surgical abdominal wall pulling device according to claim 1, wherein the elongate, generally thin member is slightly flexible.

4. A surgical abdominal wall suspending device comprising:

a pulling member;

an elongate, generally thin member forming a generally conical helix and comprising a first free end and a second end, said generally conical helix having an apex, and the second end of the elongate, generally thin member being situated at the apex of said generally conical helix and connected to said pulling member; and wherein, to suspend the abdominal wall of a patient lying on his back, (a) an incision is cut in the patient's abdominal wall, (b) the first free end of the elongate, generally thin member is inserted in the incision and the elongate, generally thin member slid in said incision until it is completely introduced in the patient's abdominal cavity, and (c) said pulling member, still located on the outside of the patient's abdominal wall is pulled upwardly to apply said generally conical helix on the inner face of the patient's abdominal wall and then to suspend the patient's abdominal wall.

* * * * *